(12) United States Patent
Akinaga et al.

(10) Patent No.: US 6,211,323 B1
(45) Date of Patent: Apr. 3, 2001

(54) HIGH MOLECULAR WEIGHT ALKYLMETHYL-ALKYLARYL SILOXANE TERPOLYMERS HAVING LOW SIH CONTENT AND METHODS FOR THEIR PREPARATION

(75) Inventors: Keiichi Akinaga, Kanagawa (JP); Qian Jane Feng, Midland; Lenin James Petroff, Bay City, both of MI (US)

(73) Assignees: Dow Corning Corporation, Midland, MI (US); Dow Corning Asia, Ltd., Tokyo (JP)

( * ) Notice: Subject to any disclaimer, the term of this patent is extended or adjusted under 35 U.S.C. 154(b) by 0 days.

(21) Appl. No.: 09/422,777

(22) Filed: Oct. 21, 1999

(51) Int. Cl.$^7$ .................................................. C08G 77/08
(52) U.S. Cl. ............................. 528/15; 528/25; 528/31; 556/456; 556/462; 556/453
(58) Field of Search .................................. 528/15, 25, 31; 556/456, 453, 462

(56) References Cited

U.S. PATENT DOCUMENTS

| | | | |
|---|---|---|---|
| 3,088,964 | 5/1963 | Ryan | 260/448.2 |
| 3,186,964 | 6/1965 | Kookootsedes et al. | 260/46.5 |
| 3,221,040 | 11/1965 | Clarence | 260/448.2 |
| 3,419,593 | 12/1968 | Willing | 260/448.2 |
| 5,035,748 * | 7/1991 | Burow et al. | 106/499 |
| 5,384,383 | 1/1995 | Legrow et al. | 528/23 |
| 5,389,365 * | 2/1995 | LeGrow et al. | 424/78.03 |
| 5,395,956 | 3/1995 | Haines et al. | 556/451 |
| 5,516,870 | 5/1996 | Biggs et al. | 528/15 |
| 5,554,708 | 9/1996 | Biggs et al. | 528/23 |
| 6,133,370 * | 10/2000 | Gutek et al. | 524/588 |
| 6,136,938 * | 10/2000 | Halloran | 528/14 |

* cited by examiner

Primary Examiner—Margaret C Moore
(74) Attorney, Agent, or Firm—Timothy J. Troy

(57) ABSTRACT

The present invention relates to triorganosiloxy-endblocked poly(methyl(C6–C40alkyl)siloxane)-poly(methyl(aralkyl) siloxane)-poly(methyl(C2–C4alkyl)siloxane) terpolymers. This invention also relates to two different methods of making these terpolymers. The triorganosiloxy-endblocked poly(methyl(C6–C40alkyl)siloxane)-poly(methyl(aralkyl) siloxane)-poly(methyl(C2–C4alkyl)siloxane) terpolymers of this invention are useful as mold release agents in aluminum die cast release agents, rubber lubricants, and as high reflexive index additives for the personal care industry.

44 Claims, No Drawings

HIGH MOLECULAR WEIGHT ALKYLMETHYL-ALKYLARYL SILOXANE TERPOLYMERS HAVING LOW SIH CONTENT AND METHODS FOR THEIR PREPARATION

BACKGROUND OF THE INVENTION

Alkylaryl and alkylmethyl organosiloxanes and methods for their preparation have been disclosed in the art. For example, Ryan in U.S. Pat. No. 3,088,964 discloses an organodisiloxane having the formula $(CH_3CH(C_6H_5)CH_2(R)_2Si)_2O$ wherein each R is a monovalent hydrocarbon radical free of aliphatic unsaturation, there being no more than one $CH_3CH(C_6H_5)CH_2$— radical per Si atom, and R is preferably methyl. Ryan also discloses a process for the production of aralkyl substituted organosilicon compounds in improved yields which comprises reacting (1) alpha-methylstyrene with (2) an organosilicon compound of the formula $R_xHSiCl_{3-x}$ where R represents a monovalent hydrocarbon radical free of aliphatic unsaturation and x is an integer of from 1 to 2 inclusive, by contacting (1) and (2) in the liquid phase in the presence of a catalytic quantity of chloroplatinic acid, where R is preferably methyl. Ryan further discloses that the resulting addition product can be hydrolyzed with water.

Kookootsedes et al. in U.S. Pat. No. 3,186,964 disclose a composition of matter consisting essentially of a toluene soluble copolymer of (1) from 10 to 90 mole percent polymeric units of the formula $(C_6H_5R—)(CH_3)SiO$, wherein R is an alkylene radical of from 2 to 3 inclusive carbon atoms such as ethylene or propylene, and (2) from 10 to 90 mole percent polymeric units of the formula $(CH_3)(R')SiO$ wherein R' is an alkyl radical of from 2 to 3 inclusive carbon atoms, where R' is preferably ethyl. Kookootsedes et al. further discloses several methods of preparing these siloxane copolymers, the preferred method being to first effect a reaction between alpha-methylstyrene and some of the silicon-bonded hydrogen atoms in a methylhydrogensiloxane, from 0.1 to 0.9 mole percent of alpha-methylstyrene per mole of methylhydrogensiloxane is used in the presence of chloroplatinic acid as the catalyst, the addition reaction resulting in the attachment of 2-phenylpropyl groups to some of the silicon atoms having hydrogen attached thereto, the reaction being carried out at temperatures of from 70 to 175° C. After the first reaction is completed, a reaction is then effected between either ethylene and/or propylene and the remaining silicon-bonded hydrogen atoms in the copolymer, preferably an excess of ethylene and/or propylene is used so that the SiH content of the copolymer is reduced to a very small value. It is further disclosed that this reaction is also best carried out in the presence of chloroplatinic acid at temperatures of from 75 to 200° C.

Pater in U.S. Pat. No. 3,221,040 discloses a copolymeric organosiloxane oil of the formula $R_3SiO((CH_3)_2SiO)_x(CH_3(C_2H_5)SiO)_w(C_6H_4(R^1)-C_2H_4(CH_3)SiO)_ySiR_3$ wherein R is a hydrocarbyl group, preferably methyl, $R^1$ is selected from the class consisting of a hydrogen atom and a methyl radical, x is a number, w is a number, the sum of x and w is at least 1, y is a number of at least one, the ratio of x+w to y is from 1:1 to 3:1, and the viscosity of the copolymeric organosiloxane oil at 25° C. is from 25 centistokes to 10,000 centistokes.

Legrow et al. in U.S. Pat. No. 5,384,383 disclose pristine phenylpropylalkylsiloxanes consisting of mixtures of linear and cyclic siloxanes containing the structure

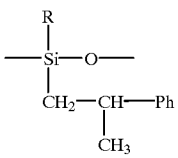

Legrow et al. further disclose that these phenylpropylalkyl-siloxanes are produced by a method comprising i) hydrolyzing a pure phenylpropylalkyldichlorosilane having a purity of greater than 99.9% and containing no detectable silicon hydride, free organics, or free inorganics and thereafter recovering the hydrolysis reaction product, and ii) equilibrating the hydrolysis reaction product with a triorganosilyl endblocker in the presence of a heterogeneous acid catalyst.

Biggs et al. in U.S. Pat. No. 5,516,870 disclose a method of making alkylmethyl cyclic siloxanes comprising (i) forming a reaction mixture containing an alpha-olefin, one or more silanol-free methylhydrogen cyclic siloxanes, and less than about 100 parts per million water, (ii) contacting the essentially anhydrous silanol-free reaction mixture with anhydrous platinum supported on carbon catalyst, (iii) agitating the mixture and catalyst to form an alkylmethyl cyclic siloxane, and (iv) continuing the reaction until the alkylmethyl cyclic siloxane is ≡SiH free; SiH free being the amount of hydrogen present as SiH within the detection limits of Fourier Transform Infrared Spectroscopy or less than one part per million.

Biggs et al. in U.S. Pat. No. 5,554,708 discloses a method of making linear triorganosiloxy endcapped methylhydrogen polysiloxanes comprising (i) forming a reaction mixture containing a silanol-free hexaorganodisiloxane, one or more silanol-free methylhydrogen cyclic siloxanes, and less than about 100 parts per million water, (ii) contacting the reaction mixture with anhydrous trifluoromethane sulfonic acid catalyst, and (iii) agitating the mixture and the catalyst at below 100° C. to form a linear triorganosiloxy endcapped methylhydrogen polysiloxane.

SUMMARY OF THE INVENTION

This invention relates to triorganosiloxy-endblocked polymethylalkylsiloxane-polyalkylarylsiloxane terpolymers.

This invention also relates to methods of preparing triorganosiloxy-endblocked polymethylalkylsiloxane-polyalkylarylsiloxane terpolymers.

It is an object of this invention to produce triorganosiloxy-endblocked polymethylalkylsiloxane-polyalkylarylsiloxane terpolymers by a highly efficient robust method which allows control of the viscosity of the terpolymer.

DETAILED DESCRIPTION OF THE INVENTION

In a first embodiment, this invention relates to a triorganosiloxy-endblocked poly(methyl(C6–40alkyl) siloxane)-poly(methyl(aralkyl)siloxane)-poly(methyl(C2–C4alkyl)siloxane) terpolymer having the formula:

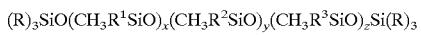

wherein each R is independently selected from the group consisting of alkyl groups, aryl groups, alkaryl groups, and aralkyl groups, $R^1$ denotes an alkyl group having from 6 to 40 carbon atoms, $R^2$ denotes an aralkyl group, $R^3$ denotes an alkyl group having from 2 to 4 carbon atoms, x has an average value of from 25 to 120, y has an average value of from 5 to 40, and z has an average value of from 0.1 to 20.

The R group is exemplified by alkyl groups such as methyl, ethyl, propyl, isopropyl, butyl, and hexyl, aryl groups such as phenyl, xenyl, or naphthyl, alkaryl groups such as tolyl or xylyl, or aralkyl groups such as benzyl, phenylethyl, or 2-phenylpropyl. The R groups can be the same or different as desired. However, it is especially preferred that R is methyl.

The alkyl groups of $R^1$ are exemplified by hexyl, octyl, decyl, dodecyl, tetradecyl, hexadecyl, octadecyl, $-C_{20}H_{41}$, $-C_{22}H_{45}$, $-C_{24}H_{49}$, $-C_{26}H_{53}$, $-C_{28}H_{57}$, $-C_{30}H_{61}$, $-C_{32}H_{65}$, $-C_{34}H_{69}$, $-C_{36}H_{73}$, $-C_{38}H_{77}$, and $-C_{40}H_{81}$. Preferably the alkyl group is selected from the group consisting of decyl, dodecyl, tetradecyl, hexadecyl, octadecyl, and $-C_{20}H_{41}$. Especially preferred is dodecyl.

The aralkyl groups of $R^2$ are exemplified by benzyl, 4-methylbenzyl, o-methoxybenzyl, p-methoxybenzyl, diphenylmethyl, 2-phenylethyl, 2-phenylpropyl, and 3-phenylpropyl, however, 2-phenylpropyl is especially preferred.

The alkyl groups of $R^3$ are exemplified by ethyl, propyl, and butyl, with ethyl being preferred.

In a second embodiment, this invention relates to a method of making a triorganosiloxy-endblocked poly(methyl(C6–C40alkyl)siloxane)-poly(methyl(aralkyl)siloxane)-poly(methyl(C2–C4alkyl)siloxane) terpolymer comprising: (i) reacting at temperature of less than or equal to 120° C. a mixture comprising (a) a linear triorganosiloxy-endblocked polymethylhydrogensiloxane, (b) an alpha-olefin having from 6 to 40 carbon atoms, and (c) a platinum-containing catalyst, (ii) reacting at temperature of less than or equal to 120° C. a mixture comprising (d) the product of (i), and (e) an unsaturated aromatic compound to form a triorganosiloxy-endblocked poly(methylalkylsiloxane)-poly(methyl(aralkyl)sitoxane)-polymethylhydro-ensiloxane terpolymer, (iii) reacting a mixture comprising (f) the triorganosiloxy-endblocked poly(methylalkylsiloxane)-poly(methyl(aralkyl)siloxane)-polymethylhydrogensiloxane terpolymer of (ii), (g) an alpha-olefin having from 6 to 40 carbon atoms, and (iv) exposing the product of (iii) to (h) an olefin having from 2 to 4 carbon atoms in the presence of (j) a platinum-containing catalyst at a temperature of from 50 to 70° C., and a pressure from atmospheric pressure to 150 psi. The mixture of steps (ii) and (iii) can further comprise a platinum-containing catalyst as described hereinbelow.

Component (a) in this invention is a linear triorganosiloxy-endblocked polymethylhydrogensiloxane. Component (a) is preferably a linear trimethylsiloxy-endblocked poly(methylhydrogensiloxane) polymer. Linear trimethylsiloxy-endblocked poly(methylhydrogensiloxane) polymers are well known in the art and may be prepared by a variety of methods.

One such method is where the trimethylsiloxy-endblocked poly(methylhydrogensiloxane) polymer is obtained by a method comprising reacting a mixture containing less than 100 ppm of water and comprising (i) a silanol-free hexaorganodisiloxane, (ii) at least one silanol-free methylhydrogen cyclic siloxane, and (iii) an anhydrous trifluoromethane sulfonic acid catalyst to form a linear triorganosiloxy-endblocked polymethylhydrogensiloxane.

"Reacting" as used with regard to this method of making Component (a) denotes simply mixing the ingredients and any optional ingredients at room temperature or heating a mixture of the ingredients and any optional ingredients at temperatures above room temperature as described herein.

For the purposes of this invention, "silanol-free" denotes that the siloxane starting materials contain no residual $\equiv$SiOH, within the limits of detection by Silicon-29 Nuclear Magnetic Resonance ($^{29}$Si NMR) and Fourier Transform Infrared Spectroscopy (FTIR), which is one part per million or less for FTIR. The resulting linear or straight-chain trimethylsiloxy-endblocked polymethylhydrogensiloxanes are fluids containing less than 0.4% branch sites by $^{29}$Si NMR, that could eventuate in the formation of an undesirable gel. A branch site frequency of 0.4 means that 1 out of 250 silicon atoms contains a branch site. Reaction conditions are mild so that branch sites are not formed during polymerization. Thus, the preferred temperature range is about 60°–70° C., although if desired, temperatures up to about 100° C. can be employed, consistent with the desire to avoid the formation of branch sites.

Component (i), the silanol-free hexaorganodisiloxanes, typically have the formula $R_3SiOSiR_3$, wherein R is an alkyl group and containing less than about 100 ppm water, such as hexamethyldisiloxane are commercially available. Silanol-free hexaorganodisiloxanes where R is an alkyl group other than methyl, can also be employed. Thus, R can be another alkyl group such as ethyl, propyl, isopropyl, butyl, or hexyl. In addition, R can be an aryl group such as phenyl, xenyl, or naphthyl; an alkaryl group such as tolyl or xylyl; or an aralkyl group such as benzyl, phenylethyl, or 2-phenylpropyl. However, it is especially preferred that R is methyl.

Component (ii) is at least one methylhydrogen cyclic siloxane, and is preferably selected from the group consisting of 1,3,5,7-tetramethylcyclotetrasiloxane (MeHSiO)$_4$, 1,3,5,7,9-pentamethylcyclopentasiloxane (MeHSiO)$_5$, and a combination of 1,3,5,7-tetramethylcyclotetrasiloxane and 1,3,5,7,9-pentamethylcyclopentasiloxane in this method of the invention, but other methylhydrogen cyclic siloxanes such as 1,3,5,7,9,11 -hexamethylcyclohexasiloxane (MeHSiO)$_6$ can also be used. In addition, the methylhydrogen cyclic siloxanes (RHSiO)$_n$ can be used alone or mixed with one another. Further, n can be 3–8, and alkyl group R may be other than methyl, such as ethyl, propyl, isopropyl, butyl, or hexyl. However, it is especially preferred that R be methyl.

Silanol-free methylhydrogen cyclic siloxane starting materials containing less than about 100 ppm water can be made by processes such as described in U.S. Pat. No. 5,395,956 (Mar. 7, 1995), which is assigned to the assignee of this invention, and incorporated herein by reference. Briefly, according to that process, an organohydrogen dichlorosilane is contacted with about a stoichiometric equivalent of water to form a hydrolyzate. The hydrolyzate is diluted in an inert solvent, and contacted with an acid rearrangement catalyst to effect formation of cyclic organohydrogen siloxanes. The cyclic organohydrogen siloxanes are separated from the inert solvent and the linear organohydrogen siloxanes. The inert solvent and linear organohydrogen siloxanes are then recycled to the process for further contact with the acid rearrangement catalyst. According to that method, hydroxyl substitution on silicon is minimized.

The mixture preferably contains 0.001–1.0 mole of hexaorganodisiloxane (i) per mole of methylhydrogen cyclic siloxane (ii). The trifluoromethane sulfonic acid catalyst (iii) can be used in amounts of 0.05–0.2% by weight, based on the weight of the mixture.

The reaction is preferably conducted at temperatures of from 60 to 70° C. Reaction time will vary, depending upon equipment being used and amount of product being produced, but typically a batch reaction requires about 3 to 5 hours for completion.

The linear trimethylsiloxy-endblocked polymethylhydrogensiloxane is typically purified by filtration, although other standard means of separating end products from reaction mixtures can be employed, such as centrifugation.

Component (a), the linear triorganosiloxy-endblocked polymethylhydrogensiloxane is typically present in amounts from 20 weight percent (wt %) to 30 wt %, and preferably present from 24 wt % to 28 wt %.

Component (b), the alpha-olefin having from 6 to 40 carbon atoms, is exemplified by 1-hexene, 2-methyl-1-pentene, 3-methyl-1-pentene, 4-methyl-1-pentene, 1-heptene, 2-methyl-1-hexene, 1-octene, 2-methyl-1-heptene, 1-nonene, 1-decene, 1-undecene, 1-dodecene, 1-tridecene, 1-tetradecene, 1-pentadecene, 1-hexadecene, 1-octadecene, 1-nonadecene, 1-eicosene, and those alpha-olefin fractions containing varying percentages of C22–C30+ alpha-olefins sold under the trademarks GULFTENE® 24–28 and GULFTENE® 30+, by Chevron Chemical Company, Houston, Tex. Preferably the alpha-olefin is selected from the group consisting of 1-decene, 1-dodecene, 1-tetradecene, 1-hexadecene, 1-octadecene, 1-eicosene, and those alpha-olefin fractions containing varying percentages of C22–C30+ alpha-olefins.

The alpha-olefin, Component (b), is typically present in amounts from 20 wt % to 30 wt %, and preferably present from 24 wt % to 28 wt %.

Component (c), the platinum-containing catalyst, is exemplified by chloroplatinic acid, alcohol modified chloroplatinic acids, olefin complexes of chloroplatinic acid, complexes of chloroplatinic acid and divinyltetramethyldisiloxane, fine platinum particles adsorbed on carbon carriers, platinum black, platinum acetylacetonate, platinous halides exemplified by $PtCl_2$, $PtCl_4$, $Pt(CN)_2$, complexes of platinous halides with unsaturated compounds exemplified by ethylene, propylene, and organovinylsiloxanes, styrene hexamethyldiplatinum, and $RhCl_3(Bu_2S)_3$. Preferably, component (c) is chloroplatinic acid.

The exact necessary amount of this catalyst component will depend on the particular catalyst utilized and is not easily predictable. However, the amount can be as low as 0.5 parts by weight of platinum for every one million parts by weight of components (a)+(b). However, preferably the catalyst is added at an amount of 1 to 500 parts per one million parts of components (a)+(b), and it is highly preferred that the amount is at 2.5 to 10 parts by weight of platinum for every one million parts by weight of (a)+(b).

Component (d), the product produced in step (i), is typically present in amounts from 40 wt % to 65 wt %, and preferably present from 45 wt % to 55 wt %.

Component (e), the unsaturated aromatic compound, is exemplified by styrene, alpha-methyl styrene, allylbenzene, eugenol, and allyl phenyl ether. Preferably Component (e) is alpha-methyl styrene.

Component (e), the unsaturated aromatic compound, is typically present in amounts from 5 wt % to 15 wt %, and preferably present from 9 wt % to 11 wt %.

Component (f) the triorganosiloxy-endblocked poly(methylalkylsiloxane)-poly(methyl(aralkyl)siloxane)-polymethylhydrogensiloxane terpolymer produced in Step (ii) is typically present in amounts from 50 wt % to 75 wt %, and preferably present from 60 wt % to 65 wt %.

Component (g), the alpha-olefin, is as described above, including preferred embodiments thereof. Component (g) is typically present in amounts from 25 wt % to 50 wt %, and preferably present from 35 wt % to 40 wt %.

The olefin (h) is exemplified by ethylene gas, propylene gas, and butylene gas. Preferably Component (h) is ethylene gas. Typically the olefinic gas is bubbled through the product of step (iii) which is typically in the form of a solution. Preferably, the product of step (iii) is exposed to the olefinic gas at a temperature from 50 to 70° C., and a pressure from atmospheric pressure to 150 psi.

Component (j), the platinum-containing catalyst, is as described above for Component (c).

Preferably Component (j) is the composition that is obtained by a method comprising reacting chloroplatinic acid with an aliphatically unsaturated organosilicon compound such as divinyltetramethyldisiloxane, as disclosed by Willing, U.S. Pat. No. 3,419,593, incorporated herein by reference, because of its easy dispersibility in organosilicon systems.

The exact necessary amount of catalyst component (j) will depend on the particular catalyst utilized and is not easily predictable. However, the amount can be as low as 0.5 parts by weight of platinum for every one million parts by weight of the product of step (iii). However, preferably the catalyst is added at an amount of 1 to 500 parts per one million parts of the product of step (iii), and it is highly preferred that the amount is at 2.5 to 10 parts by weight of platinum for every one million parts by weight of the product of step (iii).

The mixture of step (i) in this method of the invention can further comprise an antioxidant. Any of the materials known in the art to stabilize systems to undesired ambient processes such as oxidation may used. These materials are exemplified by tocopherols (e.g. Vitamin E), hydroquinones, and n-phenyl-1-naphtylamine, with n-phenyl-1-napthylamine being preferred. These antioxidants act to keep the quality of the product mixture consistent over time.

The method of this invention can further comprise adding a neutralizing agent to the linear trimethylsiloxy-endblocked polymethylhydrogensiloxane (a). The neutralizing agent is exemplified by sodium bicarbonate, ammonium carbonate, and calcium carbonate, with sodium bicarbonate being preferred. Preferably, from 1to 2 weight parts of neutralizing agent per 100 parts of Components (i)+(ii)+(iii) is used.

The method of this invention can further comprise stripping the linear trimethylsiloxy-endblocked polymethylhydrogensiloxane (a). Methods of removing volatile components are well known in the art and need no extensive delineation herein. Any method of removing volatile components can be used in the present invention, such methods exemplified by heating and/or application of a vacuum, molecular stills, rotoevaporators, and wipe film evaporators.

In a third embodiment, this invention relates to a method of making a triorganosiloxy-endblocked poly(methyl (C6–C40alkyl)siloxane)-poly(methyl(aralkyl)siloxane)-poly(methyl(C2–C4alkyl)siloxane) terpolymer comprising: (i) reacting at temperature of less than or equal to 120° C. a mixture comprising (a) a linear triorganosiloxy-endblocked polymethylhydrogensiloxane, (b) an unsaturated aromatic compound, (c) a platinum-containing catalyst, and (ii) reacting at temperature of less than or equal to 120° C. a mixture comprising (d) the product of (i), and (e) an alpha-olefin having from 6 to 40 carbon atoms to form a triorganosiloxy-endblocked poly(methylalkylsiloxane)-poly(methyl (aralkyl)siloxane)-polymethylhydrogensiloxane terpolymer, and (iii) exposing the triorganosiloxy-endblocked poly (methylalkylsiloxane)-poly(methyl(aralkyl)siloxane)-polymethylhydrogensiloxane terpolymer of (ii) to (f) an olefin having from 2 to 4 carbon atoms in the presence of (g) a platinum-containing catalyst at a temperature of from 50 to 70° C., and a pressure from atmospheric pressure to 150 psi. The mixture of step (ii) can further comprise a platinum-containing catalyst as described hereinabove.

Component (a), the linear triorganosiloxy-endblocked polymethylhydrogensiloxane is as described above in the second embodiment of this invention. Preferably Component (a) is a linear trimethylsiloxy-endblocked poly(methylhydrogensiloxane) polymer. Component (a), the linear triorganosiloxy-endblocked polymethylhydrogensiloxane is typically present in amounts from 20 weight percent (wt %) to 30 wt %, and preferably present from 24 wt % to 28 wt %.

Component (b), the unsaturated aromatic compound, is exemplified by styrene, alpha-methyl styrene, allylbenzene, eugenol, and allyl phenyl ether. Preferably Component (b) is alpha-methyl styrene. Component (b), the unsaturated aromatic compound, is typically present in amounts from 5 wt % to 15 wt %, and preferably present from 9 wt % to 11 wt %.

Component (c), the platinum-containing catalyst, is as described above in the second embodiment of this invention. Preferably, component (c) is chloroplatinic acid.

The exact necessary amount of this catalyst component will depend on the particular catalyst utilized and is not easily predictable. However, the amount can be as low as 0.5 parts by weight of platinum for every one million parts by weight of components (a)+(b). However, preferably the catalyst is added at an amount of 1 to 500 parts per one million parts of components (a)+(b), and it is highly preferred that the amount is at 2.5 to 10 parts by weight of platinum for every one million parts by weight of (a)+(b).

Component (d), the product produced in step (i), is typically present in amounts from 25 wt % to 45 wt %, and preferably present from 30 wt % to 40 wt %.

The alpha-olefin, Component (e), is as described above in the second embodiment of this invention. Preferably Component (e) is 1-dodecene. Component (c) is typically present in amounts from 55 wt % to 75 wt %, and preferably present from 60 wt % to 70 wt %.

The olefin (f) is exemplified by ethylene gas, propylene gas, and butylene gas. Preferably Component (f) is ethylene gas. Typically the olefinic gas is bubbled through the product of step (ii) which is typically in the form of a solution. Preferably, the product of step (ii) is exposed to the olefinic gas at a temperature from 50 to 70° C., and a pressure from atmospheric pressure to 150 psi.

Component (g), the platinum-containing catalyst, is as described above in the second embodiment of this invention. Preferably Component (g) is the composition that is obtained by a method comprising reacting chloroplatinic acid with an aliphatically unsaturated organosilicon compound such as divinyltetramethyldisiloxane, as described above.

The exact necessary amount of catalyst component (g) will depend on the particular catalyst utilized and is not easily predictable. However, the amount can be as low as 0.5 parts by weight of platinum for every one million parts by weight of the product of step (ii). However, preferably the catalyst is added at an amount of 1 to 500 parts per one million parts of the product of step (ii), and it is highly preferred that the amount is at 2.5 to 10 parts by weight of platinum for every one million parts by weight of the product of step (ii).

The mixture of step (i) in this method of the invention can further comprise an antioxidant. The antioxidant is as described above including preferred amounts and embodiments thereof.

This method of this invention can further comprise adding a neutralizing agent to the linear trimethylsiloxy-endblocked polymethylhydrogensiloxane (a). The neutralizing agent is exemplified by sodium bicarbonate, ammonium carbonate, and calcium carbonate, with sodium bicarbonate being preferred. Preferably, from 1 to 2 weight parts of neutralizing agent per 100 parts of Components (i)+(ii)+(iii) is used.

This method of this invention can further comprise stripping the linear trimethylsiloxy-endblocked polymethylhydrogensiloxane (a). Methods of removing volatile components are well known in the art and need no extensive delineation herein. Any method of removing volatile components can be used in the present invention, such methods exemplified by heating and/or application of a vacuum, molecular stills, rotoevaporators, and wipe film evaporators.

The triorganosiloxy-endblocked poly(methyl(C6–C40alkyl)siloxane)-poly(methylaralkylsiloxane)-poly(methyl(C2–C4alkyl)sitoxane) terpolymers of this invention are useful as mold release agents in aluminum die cast release agents, rubber lubricants, and as high reflexive index additives for the personal care industry.

EXAMPLES

Reference Example 1

Preparation of a trimethylsiloxy-endblocked poly(methylhydrogensiloxane) polymer having the average formula $(CH_3)_3SiO(CH_3HSiO)_{138}Si(CH_3)_3$ A solution of 1104.5 grams of a silanol-free hexamethyldisiloxane, 146.8 kilograms of a silanol-free mixture of 50% by weight 1,3,5,7-tetramethylcyclotetrasiloxane and 50% by weight 1,3,5,7,9-pentamethylcyclopentasiloxane, and 0.1% by weight anhydrous trifluoromethane sulfonic acid, was stirred for 4 hours at 65° C. A sample was taken and viscosity was measured as 69 mm$^2$/s (1 mm$^2$/s=1 centistoke). The mixture was held at 65° C. for an additional hour, then a sample was taken for the test of viscosity at 70 mm$^2$/s to confirm the reaction was complete. The reaction mixture was neutralized with 1.36 kilograms of NaHCO$_3$. After neutralization of the reaction mixture, neutrality was confirmed by testing the acid number. Positive-pressure filtration provided a clear liquid. The solution was stripped under reduced pressure at 120° C. for 4 hours. Analysis of the stripped product by $^{29}$Si NMR showed a degree of polymerization of 140 and viscosity of the product was 87 mm$^2$/s.

Reference Example 2

Preparation of a trimethylsiloxy-endblocked poly(methyldodecylsiloxane)-poly(methyl(2-phenylpropyl)siloxane)-polymethylhydrogensiloxane terpolymer having the average formula:

$(CH_3)_3SiO(CH_3RSiO)_{76}(CH_3R^1SiO)_{20}(MeHSiO)_2Si(CH_3)_3$ wherein R denotes dodecyl and $R^1$ denotes 2-phenylpropyl.

To a 36.1 kilogram solution of a trimethylsiloxy-endblocked polymethylhydrogensiloxane polymer having the average formula $(CH_3)_3Si(CH_3HSiO)_{98}Si(CH_3)_3$ was added 2.5 kilograms of alpha-methylstyrene and 6.9 grams of n-phenyl-1-napthylamine. The polymethylhydrogensiloxane polymer was prepared according to the method of Reference Example 1. The reactor was heated to 80° C. A 10.5 wt % solution of H$_2$PtCl$_6$ diluted in isopropyl alcohol was prepared and added to the reactor to deliver 2.5ppm Pt into the solution, resulting in an exotherm to 90° C. An additional 11.4 kilograms of alpha-methylstyrene was added slowly to maintain the reaction temperature below 120° C. After the reaction was held at 120° C. for 1 hour, 87 kilograms of 1-dodecene was added. After stirring for 1 hour at 120° C., FTIR analysis of the reaction mixture showed 99 ppm SiH. After excess 1-dodecene was stripped off at 30 mmHg at 150° C. for 5 hours from the polymer, FTIR analysis showed 76 ppm SiH and viscosity of the product was 2500 mm$^2$/s.

Reference Example 3

Preparation of a trimethylsiloxy-endblocked poly (methyldodecylsiloxane)-poly(methyl(2-phenylpropyl) siloxane)-polymethylhydrogensiloxane terpolymer having the average formula:

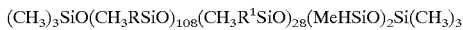

wherein R denotes dodecyl and R$^1$ denotes 2-phenylpropyl.

To a 35 kilogram solution of a trimethylsiloxy-endblocked poly(methylhydrogensiloxane) polymer having the average formula $(CH_3)_3Si(CH_3HSiO)_{138}Si(CH_3)_3$ was added 4.36 kilograms of 1-dodecene and 6.8 grams of n-phenyl-1-napthylamine. The trimethylsiloxy-endblocked poly(methylhydrogensiloxane) polymer was prepared as described in Reference Example 1. The reactor was heated to 90° C. A 10.5 wt % solution of $H_2PtCl_6$ diluted in isopropyl alcohol was prepared and added to the reactor to deliver 2.5 ppm Pt into the solution, resulting in exotherm to 108° C. An additional 30.5 kilograms of 1-dodecene was metered slowly to maintain the reactor temperature below 120° C., followed by addition of 13.6 kilograms of alpha-methylstyrene. After the reaction was held at 120° C. for 1 hour, an additional 52.3 kilograms of 1-dodecene was added. After stirring for 1 hour at 120° C., FTIR analysis of the reaction mixture showed 230 ppm SiH. After excess 1-dodecene was stripped at 30 mm Hg at 150° C. for 5 hours from the polymer, FTIR analysis of the reaction mixture showed 37 ppm SiH and viscosity of the product was 4160 mm$^2$/s.

Example 1

Preparation of a trimethylsiloxy-endblocked poly(methyl (dodecyl)siloxane)-poly(methyl(2-phenylpropyl)siloxane)-poly(methyl(ethyl)siloxane) terpolymer having the average formula:

$(CH_3)_3SiO(CH_3RSiO)_{89}(CH_3R^1SiO)_{24}(CH_3R^2SiO)_8Si(CH_3)_3$ wherein R denotes dodecyl, R$^1$ denotes 2-phenylpropyl, and R$^2$ denotes ethyl.

A 200 gram solution of a trimethylsiloxy-endblocked poly(methyl(dodecyl)siloxane)-poly(methyl(2-phenylpropyl)siloxane)-polymethylhydrogensiloxane terpolymer having the average formula $(CH_3)_3SiO(CH_3RSiO)_{89}(CH_3R^1SiO)_{24}(CH_3HSiO)_8Si(CH_3)_3$ wherein R denotes dodecyl and R$^1$ denotes 2-phenylpropyl was prepared according to the method of Reference Example 2 was diluted with 20 grams of 1-dodecene. Next a chloroplatinic acid-divinyltetramethyldisiloxane complex was added to deliver 5 ppm of platinum to the reaction mixture. Next, ethylene gas was bubbled through the solution at 50–55° C. for 1 hour at atmospheric pressure. FTIR analysis of the reaction mixture showed 7 ppm SiH.

Example 2

Preparation of a trimethylsiloxy-endblocked poly(methyl (dodecyl)siloxane)-poly(methyl(2-phenylpropyl)siloxane)-poly(methyl(ethyl)siloxane) terpolymer having the average formula:

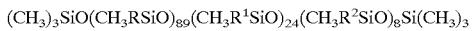

wherein R denotes dodecyl, R$^1$ denotes 2-phenylpropyl, and R$^2$ denotes ethyl.

To a 65.4 gram solution of a trimethylsiloxy-endblocked poly(methylhydrogensiloxane) polymer having the average formula $(CH_3)_3Si(CH_3HSiO)_{121}Si(CH_3)_3$ was added 8 grams of 1-dodecene and 0.01 grams of n-phenyl-1-napthylamine. The trimethylsiloxy-endblocked poly (methylhydrogensiloxane) polymer was prepared according to the method of Reference Example 1. The solution was heated to 80° C. A 3.0 wt % solution of $H_2PtCl_6$ diluted in isopropyl alcohol was prepared and added to the reactor to deliver 2.5 ppm Pt into the solution. An additional 56 grams of 1-dodecene was metered slowly to maintain the reactor temperature below 120° C., followed by addition of 25 grams of alpha-methylstyrene. After the reaction was held at 120° C. for 1 hour, an additional 95.7 grams 1-dodecene was added. After stirring for 1 hour at 120° C., FTIR analysis of the reaction mixture showed 160 ppm SiH. The reaction was cooled to 50° C. and then a chloroplatinic acid-divinyltetramethyldisiloxane complex containing about 5 ppm platinum was added. Next, ethylene gas was bubbled through the solution at 55–65° C. for 1 hour. FTIR analysis showed 5 ppm SiH.

That which is claimed is:

1. A triorganosiloxy-endblocked poly(methyl (C6–C40alkyl)siloxane)-poly(methyl(aralkyl)siloxane)-poly(methyl(C2–C4alkyl)siloxane) terpolymer having the formula:

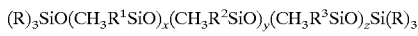

wherein each R is independently selected from the group consisting of alkyl groups, aryl groups, alkaryl groups, and aralkyl groups, R$^1$ denotes an alkyl group having from 6 to 40 carbon atoms, R$^2$ denotes an aralkyl group, R$^3$ denotes an alkyl group having from 2 to 4 carbon atoms, x has an average value of from 25 to 120, y has an average value of from 5 to 40, and z has an average value of from 0.1 to 20.

2. A terpolymer according to claim 1, wherein R is methyl.

3. A terpolymer according to claim 1, wherein R$^1$ is selected from the group consisting of decyl, dodecyl, tetradecyl, hexadecyl, octadecyl, and -C$_{20}$H$_{41}$.

4. A terpolymer according to claim 2, wherein R$^1$ is selected from the group consisting of decyl, dodecyl, tetradecyl, hexadecyl, octadecyl, and -C$_{20}$H$_{41}$.

5. A terpolymer according to claim 2, wherein R$^1$ is dodecyl.

6. A terpolymer according to claim 1, wherein R$^2$ is selected from the group consisting of benzyl, 4-methylbenzyl, o-methoxybenzyl, p-methoxybenzyl, diphenylmethyl, 2-phenylethyl, 2-phenylpropyl, and 3-phenylpropyl.

7. A terpolymer according to claim 4, wherein R$^2$ is selected from the group consisting of benzyl, 4-methylbenzyl, o-methoxybenzyl, p-methoxybenzyl, diphenylmethyl, 2-phenylethyl, 2-phenylpropyl, and 3-phenylpropyl.

8. A terpolymer according to claim 5, wherein R$^2$ is 2-phenylpropyl.

9. A terpolymer according to claim 1, wherein R$^3$ is ethyl.

10. A terpolymer according to claim 2, wherein R$^3$ is ethyl.

11. A terpolymer according to claim 4, wherein R$^3$ is ethyl.

12. A terpolymer according to claim 5, wherein R$^3$ is ethyl.

13. A terpolymer according to claim 7, wherein $R^3$ is ethyl.

14. A terpolymer according to claim 8, wherein $R^3$ is ethyl.

15. A method of making a triorganosiloxy-endblocked poly(methyl(C6–C40alkyl)siloxane)-poly(methyl(aralkyl)siloxane)-poly(methyl(C2–C4alkyl)siloxane) terpolymer comprising:
   (i) reacting at temperature of less than or equal to 120° C. a mixture comprising:
      (a) a linear triorganosiloxy-endblocked polymethylhydrogensiloxane;
      (b) an alpha-olefin having from 6 to 40 carbon atoms; and
      (c) a platinum-containing catalyst
   (ii) reacting at temperature of less than or equal to 120° C. a mixture comprising:
      (d) the product of (i); and
      (e) an unsaturated aromatic compound to form a triorganosiloxy-endblocked poly(methylalkylsiloxane)-poly(methyl(aralkyl)siloxane)-polymethylhydrogensiloxane terpolymer;
   (iii) reacting a mixture comprising:
      (f) the triorganosiloxy-endblocked poly(methylalkylsiloxane)-poly(methyl(aralkyl)siloxane)-polymethylhydrogensiloxane terpolymer of (ii);
      (g) an alpha-olefin having from 6 to 40 carbon atoms; and
   (iv) exposing the product of (iii) to (h) an olefin having from 2 to 4 carbon atoms in the presence of (j) a platinum-containing catalyst at a temperature of from 50 to 70° C., and a pressure from atmospheric pressure to 150 psi.

16. A method according to claim 15, wherein the linear triorganosiloxy-endblocked polymethylhydrogensiloxane of (a) is obtained by a method comprising reacting at a temperature of below 100° C. a mixture containing less than 100 ppm water comprising:
   (i) a silanol-free hexaorganodisiloxane;
   (ii) at least one silanol-free methylhydrogen cyclic siloxane; and
   (iii) an anhydrous trifluoromethane sulfonic acid catalyst.

17. A method according to claim 15, wherein
   (b) and (g) are each selected from the group consisting of 1-decene, 1-dodecene, 1-tetradecene, 1-hexadecene, 1-octadecene, 1-eicosene, and those alpha-olefin fractions containing varying percentages of C22–C30 alpha-olefins,
   (c) is chloroplatinic acid,
   (e) is selected from the group consisting of styrene, alpha-methyl styrene, allylbenzene, eugenol, and allyl phenyl ether,
   (h) is ethylene gas, and
   (j) is a composition obtained by a method comprising reacting chloroplatinic acid with divinyltetramethyldisiloxane.

18. A method according to claim 17, wherein (b) and (g) are each 1-dodecene and (e) is alpha-methyl styrene.

19. A method according to claim 16, wherein
   (b) and (g) are each selected from the group consisting of 1-decene, 1-dodecene, 1-tetradecene, 1-hexadecene, 1-octadecene, 1-eicosene, and those alpha-olefin fractions containing varying percentages of C22–C30 alpha-olefins,
   (c) is chloroplatinic acid,
   (e) is selected from the group consisting of styrene, alpha-methyl styrene, allylbenzene, eugenol, and allyl phenyl ether,
   (h) is ethylene gas, and
   (j) is a composition obtained by a method comprising reacting chloroplatinic acid with divinyltetramethyldisiloxane.

20. A method according to claim 19, wherein (b) and (g) are each 1-dodecene and (e) is alpha-methyl styrene.

21. A method according to claim 15, wherein the mixture of step (i) further comprises an antioxidant.

22. A method according to claim 18, wherein the mixture of step (i) further comprises an antioxidant.

23. A method according to claim 20, wherein the mixture of step (i) further comprises an antioxidant.

24. A method according to claim 16, wherein the method further comprises adding a neutralizing agent to (a).

25. A method according to claim 16, wherein the method further comprises stripping (a).

26. A method according to claim 24, wherein the method further comprises stripping (a).

27. A method according to claim 15, wherein the method further comprises stripping the product of step (iv).

28. A method according to claim 18, wherein the method further comprises stripping the product of step (iv).

29. A method according to claim 20, wherein the method further comprises stripping the product of step (iv).

30. A method of making a triorganosiloxy-endblocked poly(methyl(C6–C40alkyl)siloxane)-poly(methyl(aralkyl)siloxane)-poly(methyl(C2–C4alkyl)siloxane) terpolymer comprising:
   (i) reacting at temperature of less than or equal to 120° C. a mixture comprising:
      (a) a linear triorganosiloxy-endblocked polymethylhydrogensiloxane;
      (b) an unsaturated aromatic compound;
      (c) a platinum-containing catalyst; and
   (ii) reacting at temperature of less than or equal to 120° C. a mixture comprising:
      (d) the product of (i); and
      (e) an alpha-olefin having from 6 to 40 carbon atoms to form a triorganosiloxy-endblocked poly(methylalkylsiloxane)-poly(methyl(aralkyl)siloxane)-polymethylhydrogensiloxane terpolymer; and
   (iii) exposing the triorganosiloxy-endblocked poly(methylalkylsiloxane)-poly(methyl(aralkyl)siloxane)-polymethylhydrogensiloxane terpolymer of (ii) to (f) an olefin having from 2 to 4 carbon atoms in the presence of (g) a platinum-containing catalyst at a temperature of from 50 to 70° C., and a pressure from atmospheric pressure to 150 psi.

31. A method according to claim 30, wherein the linear triorganosiloxy-endblocked polymethylhydrogensiloxane of (a) is obtained by a method comprising reacting at a temperature of below 100° C. a mixture containing less than 100 ppm water comprising:
   (i) a silanol-free hexaorganodisiloxane;
   (ii) at least one silanol-free methylhydrogen cyclic siloxane; and
   (iii) an anhydrous trifluoromethane sulfonic acid catalyst.

32. A method according to claim 30, wherein
   (b) is selected from the group consisting of styrene, alpha-methyl styrene, allylbenzene, eugenol, and allyl phenyl ether, (c) is chloroplatinic acid, (e) is selected from the group consisting of 1-decene, 1-dodecene, 1-tetradecene, 1-hexadecene, 1-octadecene, 1-eicosene, and those alpha-olefin fractions containing varying percentages of C22–C30 alpha-olefins, (f) is ethylene gas, and (g) is a composition obtained by a method comprising reacting chloroplatinic acid with divinyltetramethyldisiloxane.

33. A method according to claim 32, wherein (b) is alpha-methyl styrene and (e) is 1-dodecene.

34. A method according to claim 31, wherein (b) is selected from the group consisting of styrene, alpha-methyl styrene, allylbenzene, eugenol, and allyl phenyl ether, (c) is chloroplatinic acid, (e) is selected from the group consisting of 1-decene, 1-dodecene, 1-tetradecene, 1-hexadecene, 1-octadecene, 1-eicosene, and those alpha-olefin fractions containing varying percentages of C22–C30 alpha-olefins, (f) is ethylene gas, and (g) is a composition obtained by a method comprising reacting chloroplatinic acid with divinyltetramethyldisiloxane.

35. A method according to claim 34, wherein (b) is alpha-methyl styrene and (e) is 1-dodecene.

36. A method according to claim 30, wherein the mixture of step (i) further comprises an antioxidant.

37. A method according to claim 33, wherein the mixture of step (i) further comprises an antioxidant.

38. A method according to claim 35, wherein the mixture of step (i) further comprises an antioxidant.

39. A method according to claim 31, wherein the method further comprises adding a neutralizing agent to (a).

40. A method according to claim 31, wherein the method further comprises stripping (a).

41. A method according to claim 39, wherein the method further comprises stripping (a).

42. A method according to claim 30, wherein the method further comprises stripping the product of step (iii).

43. A method according to claim 33, wherein the method further comprises stripping the product of step (iii).

44. A method according to claim 35, wherein the method further comprises stripping the product of step (iii).

* * * * *